(12) United States Patent
Takahashi

(10) Patent No.: US 11,045,153 B2
(45) Date of Patent: Jun. 29, 2021

(54) DEVICE FOR ACQUIRING PULSE HEIGHT SPECTRUM, METHOD FOR ACQUIRING PULSE HEIGHT SPECTRUM, PROGRAM FOR ACQUIRING PULSE HEIGHT SPECTRUM, AND RADIATION IMAGING APPARATUS

(71) Applicant: Hitachi, Ltd., Tokyo (JP)

(72) Inventor: Isao Takahashi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/628,253

(22) PCT Filed: May 23, 2018

(86) PCT No.: PCT/JP2018/019814
§ 371 (c)(1),
(2) Date: Jan. 2, 2020

(87) PCT Pub. No.: WO2019/017069
PCT Pub. Date: Jan. 24, 2019

(65) Prior Publication Data
US 2020/0170586 A1 Jun. 4, 2020

(30) Foreign Application Priority Data
Jul. 20, 2017 (JP) .............................. JP2017-141057

(51) Int. Cl.
*A61B 6/03* (2006.01)
*G01T 1/36* (2006.01)
(Continued)

(52) U.S. Cl.
CPC .............. *A61B 6/03* (2013.01); *A61B 6/4241* (2013.01); *G01T 1/36* (2013.01); *G01T 1/15* (2013.01)

(58) Field of Classification Search
CPC ....... A61B 6/032; A61B 6/4241; A61B 6/037; A61B 6/4266; A61B 6/03; G01T 1/36; G01T 1/15
See application file for complete search history.

(56) References Cited

U.S. PATENT DOCUMENTS 10,383,585 B2 * 8/2019 Konno ................. G01N 23/046
2009/0140159 A1 6/2009 Tomita
(Continued)

FOREIGN PATENT DOCUMENTS

JP 2007-256096 A 10/2007
JP 2012-225923 A 11/2012
(Continued)

OTHER PUBLICATIONS

International Search Report with English translation and Written Opinion issued in corresponding application No. PCT/JP2018/019814 dated Aug. 14, 2018.
(Continued)

*Primary Examiner* — David P Porta
*Assistant Examiner* — Fani Boosalis
(74) *Attorney, Agent, or Firm* — Foley & Lardner LLP

(57) ABSTRACT

A highly accurate pulse height spectrum is generated within a short amount of time, further cost of a radiation imaging apparatus being reduced by employing a detector that performs calibration using the pulse height spectrum. Provided is a pulse height spectrum acquisition device of a radiation detector including multiple counting units for counting a detected signal obtained by detecting incident X-rays, when a value of the detected signal is equal to or larger than a threshold, and for outputting a count value of each counting unit. This device is provided with a threshold setter configured to set to a first counting unit, a first threshold V1 as a threshold for a first measurement, along with setting to a
(Continued)

second counting unit, a second threshold V2 larger than the first threshold V1, and to set to the first counting unit, a reconfigured threshold V1' as the threshold for a second measurement, the reconfigured threshold V1' being different from the first threshold V1, a measurement controller configured to perform multiple measurements, and a pulse height spectrum generator configured to generate a pulse height spectrum for the first threshold V1 of the first counting unit, on the basis of a difference in the count values from the first counting unit and the second counting unit, obtained by the multiple measurements performed by the measurement controller.

7 Claims, 10 Drawing Sheets

(51) Int. Cl.
*A61B 6/00* (2006.01)
*G01T 1/15* (2006.01)

(56) References Cited

U.S. PATENT DOCUMENTS

| | | |
|---|---|---|
| 2012/0184848 A1 | 7/2012 | Ohi |
| 2012/0268105 A1 | 10/2012 | Mann |
| 2015/0185332 A1 | 7/2015 | Herrmann |
| 2015/0192681 A1 | 7/2015 | Cho |
| 2016/0305818 A1 | 10/2016 | Ichikawa |
| 2016/0370475 A1 | 12/2016 | Kawata |

FOREIGN PATENT DOCUMENTS

| | | |
|---|---|---|
| JP | 2015-184119 A | 10/2015 |
| JP | 2015-528901 A | 10/2015 |
| WO | WO-2011/039819 A1 | 4/2011 |
| WO | WO-2015/087663 A1 | 6/2015 |

OTHER PUBLICATIONS

International Preliminary Report on Patentability issued in corresponding International Application No. PCT/JP2018/019814 dated Jan. 30, 2020.

* cited by examiner

DEVICE FOR ACQUIRING PULSE HEIGHT SPECTRUM, METHOD FOR ACQUIRING PULSE HEIGHT SPECTRUM, PROGRAM FOR ACQUIRING PULSE HEIGHT SPECTRUM, AND RADIATION IMAGING APPARATUS

TECHNICAL FIELD

The present invention relates to a pulse height spectrum acquisition device, a pulse height spectrum acquisition method, a pulse height spectrum acquisition program, and a radiation imaging apparatus. More particularly, the present invention relates to the pulse height spectrum acquisition device, the pulse height spectrum acquisition method, the pulse height spectrum acquisition program, and the radiation imaging apparatus, for generating a pulse height spectrum on the basis of a detection result from a photon-counting type X-ray detector.

BACKGROUND ART

In medical-use radiation imaging apparatus utilizing X-rays, such as computed tomography (CT) scanners, conventionally, a detector detects X-rays emitted from an X-ray source and passing through an object, and acquires information of X-ray attenuation caused by the object, thereby visualizing the internal state of the object to provide it for diagnosis.

Currently used typical whole-body CT scanners generate X-rays from an X-ray tube to which high voltage has been applied, and scintillators detect the X-rays passing through the object. The X-rays detected by the scintillators are converted into fluorescence, and optical devices such as a photodiodes read out this fluorescence to output the fluorescence in the form of electrical signals. This detector system is employed in, what is called, a current mode (or an integration mode). In other words, a measured value indicates a total amount of the electrical signals generated during a certain time span, e.g., within a millisecond, but each of X-ray photons is not measured individually. Therefore, for example, detection of one X-ray photon of energy 100 keV and detection of two X-ray photons of energy 50 keV each, may bring about identical measurement results.

In recent years, in this type of radiation imaging apparatus, it has become very active to employ the detector system in a pulse mode, instead of the current mode, that is, detecting the X-ray photons passing through the object in the pulse mode, separately one by one, so as to implement more accurate diagnostic equipment. Detection of each X-ray photon separately allows acquisition of energy information of the X-ray photons, which has been unavailable in conventional computed tomography. Therefore, in the field of computed tomography, this is referred to as photon-counting CT (PCCT) or other similar names, as next-generation equipment, and it is expected that such equipment should bring about material decomposition or low exposure that has not been feasible in the conventional computed tomography.

When it is attempted to employ the detector in the pulse mode, there may be a major problem that X-ray photons are prone to have extremely high incident rate. In normal whole-body CT scanners, sometimes X-ray photons on the order of $10^9$ per second per square millimeter of the detector ($10^9$ cps/mm$^2$) at the maximum are detected.

The typical size of pixel in the detector of a computed tomography scanner is on the order of 1 mm square. For example, assuming that 50 nanoseconds are required for the detector system to process a signal of one X-ray photon, there is a possibility that during signal processing of a particular X-ray photon, tens of signals of other X-ray photons may arrive, or the signal processing may be performed on erroneously recognized signals of two or more X-ray photons, instead of the signal of a single X-ray photon (what is called, pile up). This state indicates that detector is experiencing saturation, and once the detector is saturated, it is not possible to count the X-ray photons properly, or to obtain accurate energy information.

To address this problem, X-ray photons may be counted only by determining larger or smaller than thresholds provided in advance, without precisely measuring the energy of the X-ray photons one by one, so as to reduce the signal processing time on the X-ray photons. Specifically, in the PCCT, an output from the X-ray detector that has detected radiation (X-rays) is compared with predetermined thresholds by using comparators, and it is counted how many photons having energy equal to or larger than the energy corresponding to these thresholds are detected per a unit time.

As one method to calibrate what energy is associated with the provided threshold, there is a method to allow entrance of X-rays or gamma-rays having characteristic energy, and on the basis of a result of counting in the detector, a pulse height (energy) spectrum of the count rate of X-ray signals per unit time is generated, thereby obtaining relations between the threshold and the energy. By way of example, Patent Literature 1 discloses that following Equation is established, where the number of counts (count rate) at a predetermined threshold pulse height $V_n$ is $C(V_n)$, and the number of counts (count rate) at a predetermined pulse height $V_n$, that is, the pulse height spectrum is $c(V_n)$:

[1]
$$c(V_n) = C(V_{n-1}) - C(V_n) \qquad (1)$$

In other words, the radiation counting equipment disclosed by Patent Literature 1 obtains from a difference between $C(V_{n-1})$ and $C(V_n)$, the number of counts (count rate) $c(V_n)$ at the predetermined pulse height $V_n$, i.e., the pulse height spectrum, as a result of pulse height analysis. That is, a difference of count rates between the thresholds is detected, and the count rates associated with the respective thresholds are calculated, thereby generating the pulse height spectrum. There is disclosed that by detecting a difference between the count rates of a plurality of thresholds, count rates respectively associated with the thresholds, are calculated, and the pulse height spectrum is generated.

PRIOR ART DOCUMENT

Patent Literature

Patent Literature 1
Japanese Unexamined Patent Application Publication No. 2015-184119

DISCLOSURE OF THE INVENTION

Problems to be Solved by the Invention

In the method for generating the pulse height spectrum of the radiation counting equipment as disclosed in Patent Literature 1, the count rates $C(V_{n-1})$ and $C(V_n)$ are obtained by separate measurements, causing that both values may have statistical errors independently. If it is attempted to obtain c ($V_n$) with high accuracy in generating the pulse height spectrum, in particular when the $C(V_{n-1})$ is nearly equal to $C(V_n)$, it is necessary to continue measurement to obtain the difference $c(V_n)$ until achieving a value of statistical significance, resulting in that long measuring time is needed. On the other hand, as for the radiation detector, calibration is performed on the basis of the pulse height spectrum in some cases, and the time needed for the calibration may lead to cost increase of a system that employs this detector.

The present invention has been made in view of the situation above, and an objective of the present invention is to generate a highly accurate pulse height spectrum within a short amount of time, and in addition, the present invention aims at reducing cost of the radiation imaging apparatus employing the detector that performs the calibration by using the pulse height spectrum.

Means for Solving the Problems

In order to solve the problems described above, the present invention provides the following means. One aspect of the present invention provides a pulse height spectrum acquisition device of a radiation detector including a plurality of counting units for counting a detected signal obtained by detecting incident X-rays, when a value of the detected signal is equal to or larger than a threshold, and for outputting a count rate of each counting unit, the pulse height spectrum acquisition device comprising, a threshold setter configured to set to a first counting unit, a first threshold V1 as a threshold for a first measurement, along with setting to a second counting unit, a second threshold V2 larger than the first threshold V1, and to set a reconfigured first threshold V1' as the threshold for a second measurement, the reconfigured first threshold being different from the first threshold V1, a measurement controller configured to perform the first measurement and the second measurement, and a pulse height spectrum generator configured to generate a pulse height spectrum for the first threshold V1 of the first counting unit, on the basis of a difference between a count rate from the first counting unit and the second counting unit obtained by the first measurement performed by the measurement controller, and a count rate from the first counting unit and the second counting unit obtained by the second measurement.

Advantage of the Invention

According to the present invention, the highly accurate pulse height spectrum is generated within a short amount of time, and further cost of the radiation imaging apparatus can be reduced which employs the detector that performs calibration by using the pulse height spectrum.

BEST MODE FOR CARRYING OUT THE INVENTION

There will now be described one embodiment of the present invention with reference to the accompanying drawings. The pulse height spectrum acquisition device relating to the present invention is to acquire pulse height spectra of a radiation detector having a plurality of counting units, each counting a detected signal of incoming X-rays, when the detected signal being equal to or larger than thresholds, and to output count values. The pulse height spectrum acquisition device relating to the present invention, includes a threshold setter configured to set to a first counting unit, a first threshold V1 as a threshold for a first measurement, along with setting to a second counting unit, a second threshold V2 larger than the first threshold V1, and to set to the first counting unit a reconfigured first threshold V1' as the threshold for a second measurement, the reconfigured first threshold being different from the first threshold V1, a measurement controller configured to perform the first measurement and the second measurement, and a pulse height spectrum generator configured to generate the pulse height spectrum for the first threshold V1 of the first counting unit, on the basis of a difference between the count value from the first counting unit and the second counting unit obtained by the first measurement performed by the measurement controller, and the count value from the first counting unit and the second counting unit obtained by the second measurement. According to the pulse height spectrum acquisition device with the configuration above, a highly accurate pulse height spectrum can be generated within a short period of time, and further, cost of a radiation imaging apparatus can be reduced, which employs the detector that performs calibration by using the pulse height spectrum.

There will be described embodiments of the present invention more specifically in the following.

First Embodiment

As one example of the radiation imaging apparatus relating to an embodiment of the present invention, an X-ray CT scanner, in particular, a PCCT scanner will be described with reference to the accompanying drawings.

Figure 1:
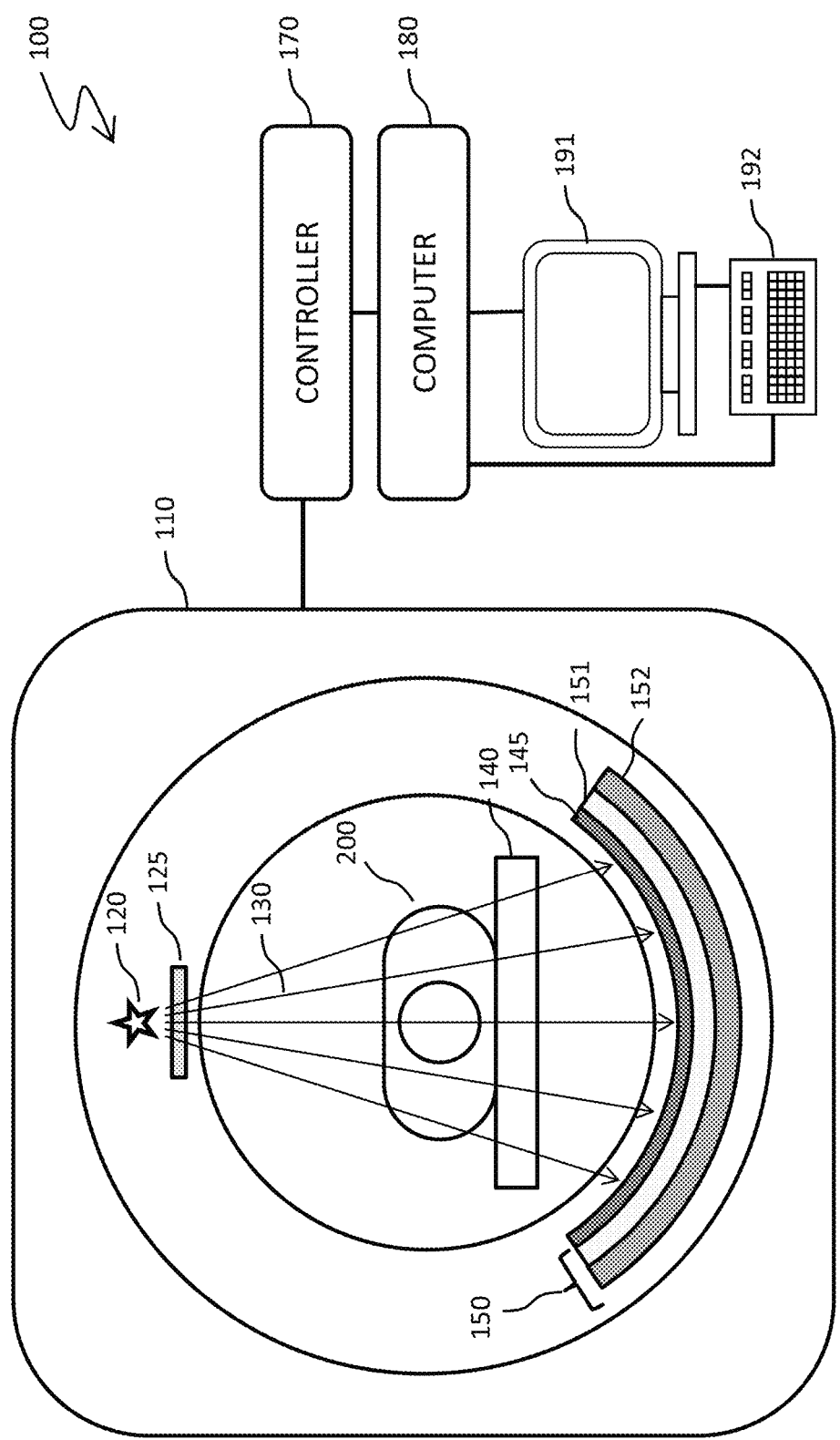
FIG. 1 is a block diagram schematically illustrating a PCCT scanner relating to the first embodiment of the present invention.

As shown in FIG. 1, the PCCT scanner is provided with an imaging system including an X-ray source 120, an X-ray detector 150, a gantry rotor 110 placing the X-ray source 120 and the X-ray detector 150 in a manner opposed to each other and rotating about a predetermined rotation axis, a table 140, a controller 170 for processing signals acquired by the X-ray detector 150 along with controlling the operations of the imaging system, and a computer 180 for creating reconstructed images on the basis of the data obtained by the X-ray detector 150.

By way of example, an X-ray tube can be employed as the X-ray source 120. The X-ray source 120 allows electron beams accelerated by tube voltage to hit a target material such as tungsten and molybdenum, to generate X-rays from the hit position (focal point), thereby emitting X-ray photons. A filter 125 is provided in proximity to the X-ray source 120. The filter 125 adjusts a flux of the X-ray photons 130 and an energy distribution thereof, which are emitted from the X-ray source 120. Therefore, after the flux and the energy distribution of the X-ray photons emitted from the X-ray source 120 are adjusted, a part thereof is absorbed by an object 200, in response to a material distribution within the object, and another part the X-ray photons passes through the object 200 and detected by the X-ray detector 150 that will be described below.

On the gantry rotor 110, the X-ray source 120 and the X-ray detector 150 are placed in a manner opposed to each other, and the gantry rotor rotates about a predetermined rotation axis. There is provided an aperture at the center of the gantry rotor 110 to place the object 200 therein, and a table 140 is arranged in the aperture to lay the object 200 thereon. The table 140 and the gantry rotor 110 are movable in predetermined directions relatively. Generally, CT scanners acquire data from all the directions, and the gantry rotor 110 rotates at a predetermined speed, allowing the X-ray source 120 and the X-ray detector 150 to rotate around the object 200, so as to acquire data. Typically, the rotation speed is approximately one to four revolutions per second. The time required to accumulate data for acquiring projection data (one view) from one direction is typically on the order of 0.1 to 1 milliseconds.

The X-ray detector 150 is provided with a detection unit 151 configured to detect the X-ray photons entering the X-ray detector 150, and to output detected signals in response to energy of thus detected X-ray photons, and a signal processor 152 configured to collect and process the detected signals output from the detection unit 151. The detected signals of the X-ray photons output from the detection unit 151 are subjected to pulse-mode processing by more than one signal processors 152, and then counted. In this example, the term "counting" described here may include a meaning to acquire energy information, in addition to counting the detected X-ray photons. Detection of X-rays having been scattered by the object 200 may generate undesirable signals, and therefore, preferably, a collimator 145 is placed in front of the detection unit 151 when viewed from the X-ray source 120 side, so as to block the scattered X-rays. Details of the X-ray detector 150 will be described below.

According to instructions from the computer 180, the controller 170 controls the gantry rotor 110, the X-ray source 120, the table 140, the X-ray detector 150, and other components, performs predetermined processing on the signals that are detected and collected by the X-ray detector 150, and transfers the processed signals to the computer 180.

Figure 2:
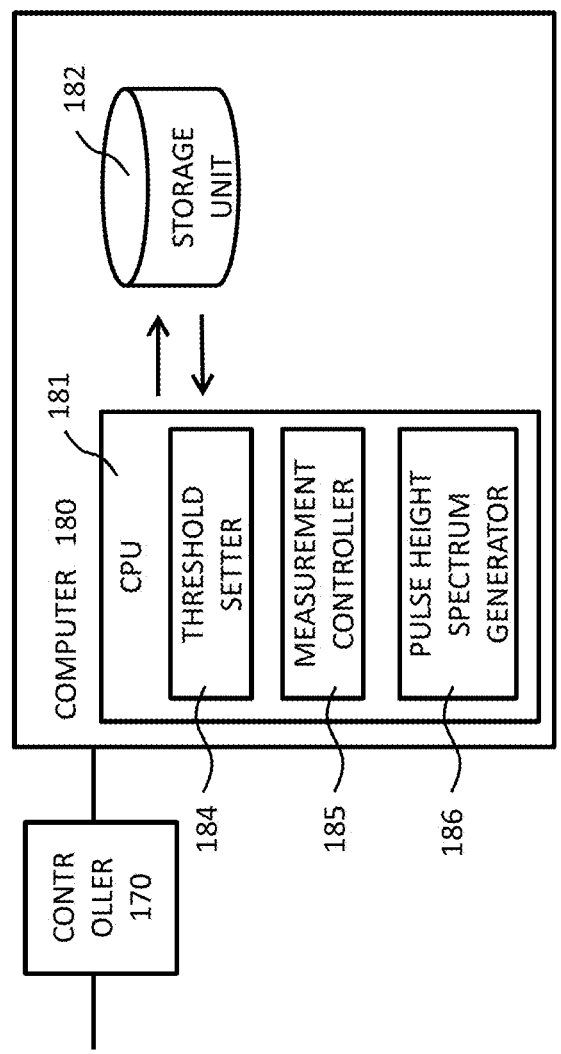
FIG. 2 is a block diagram showing a schematic configuration of a computer in the PCCT scanner relating to the first embodiment of the present invention.

As shown in FIG. 2, the computer 180 is provided with a CPU 181 and a storage unit 182. Also as shown in FIG. 2, the CPU 181 implements functions of the threshold setter 184, the measurement controller 185, and the pulse height spectrum generator 186. The computer 180 stores in the storage unit 182, the signals acquired via the controller 170 from the signal processor 152 of the X-ray detector 150, and on the basis of those signals and other data, the computer reconstructs tomographic images of the subject and reconstructed images are created.

The threshold setter 184 provides thresholds respectively in the plurality of counting units 351 to 354 (see FIG. 6) held by a channel 165 of a sub-pixel 21 of the detector, which will be described below. Details of the threshold setting according to the threshold setter 184 will be described later. The measurement controller 185 generates control signals to perform measurement (imaging) of the object, further generates control signals to perform necessary measurements to generate a pulse height spectrum, and then outputs those control signals to the controller 170. The pulse height spectrum generator 186 receives via the controller 170 the outputs from the detector, obtained by the measurement performed based on the control signals for the measurement generated by the measurement controller 185, and generates the pulse height spectrum on the basis of the outputs thus received.

The computer 180 is connected to a display unit 191 and to an input unit 192, and the reconstructed images created by the CPU 181 functioning as the image generator (not illustrated) are displayed on the display unit 191, according to the instruction from the CPU 181. The input unit 192 accepts entries of imaging conditions and other information for the X-ray CT scanner, i.e., parameters necessary for data collection, such as a value of voltage applied to the X-ray source 120 from a high-voltage source (not illustrated) and tube current, and velocity and other values of the rotating operation of the X-ray source 120. The display unit 191 is capable of displaying the parameters and the values thereof, and soon, input from the input unit 192.

A part or all of the controller 170 and the computer 180 may be constructed as a system containing a memory and a main storage, and functions of the components constituting the controller 170 and the computer 180 can be implemented by the CPU that loads programs into the memory, the programs being stored in advance in the storage unit, and then executing the programs. A part or all of the functions may also be configured by hardware such as ASIC (Application Specific Integrated Circuit) and FPGA (Field Programmable Gate Array).

Next, the X-ray detector 150 will be described. The X-ray detector 150 is provided with a detection unit 151 comprising a two-dimensional array of multiple pixels 20 and detecting X-ray photons per pixel to output signals, and a signal processor 152 configured to collect and process the signals output from each of the pixels 20 of the detection unit 151.

Figure 3:
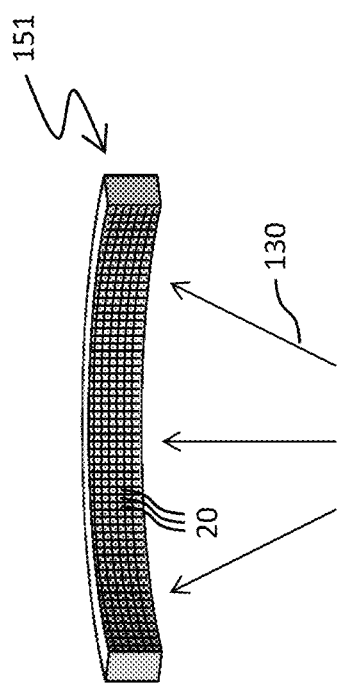
FIG. 3 is a perspective view schematically illustrating an X-ray detector relating to the first embodiment of the present invention.

As shown in FIG. 3, the detection unit 151 is one of the units of the X-ray detector 150, and comprises an array of multiple pixels 20 for detecting incoming X-ray photons. The X-ray photons 130 passing through the object 200 enter each of the pixels 20, and the X-ray photons are counted. The number of the pixels included in the detection unit 151 may be 892 in the longitudinal direction and 64 in the transverse direction.

As shown in FIG. 3, the detection unit 151 is provided in the form of arc, setting the X-ray source 120 as the arc-center approximately, and along with the rotation of the gantry rotor 110, the detection unit 151 rotates with keeping the positional relation with the X-ray source 120. It is to be noted that the arrangement of the pixels 20 in the example as shown in FIG. 3 are depicted in a manner that forms an approximate curved surface. However, in many cases, the pixels may form a flat surface without curvature, and sometimes, the arrangement of the pixels 20 in the detection unit 151 may form a polygonal shape. The X-ray photons passing through the object 200 enter each of the pixels 20, and they are counted.

In order to eliminate the X-ray photons scattered by the object 200, the collimator 145 (see FIG. 1) is placed on the pixels 20, on the X-ray source 120 side. The collimator 145 may be a two-dimensional square hole collimator, having the same pitch and shape as the pixels 20, or it may be one-dimensional slit collimator.

In the detection unit 151, each of the pixels 20 comprises a group of sensing elements referred to as sub-pixels 21, where a plurality of sensing elements are provided in an array. This group of sensing elements constitutes the pixel 20 serving as one unit of the X-ray detector 150. In other words, one pixel 20 has a configuration divided into multiple sub-pixels 21. This configuration allows reduction of the count rate per processing circuit. The sub-pixels 21 included in the pixel 20 are sensing elements in a mode of, what is called, photon counting, and they detect incoming X-ray photons, and count the X-ray photons, with separating them into four energy ranges, for instance, in the signal processor 152 being connected.

Figure 4:
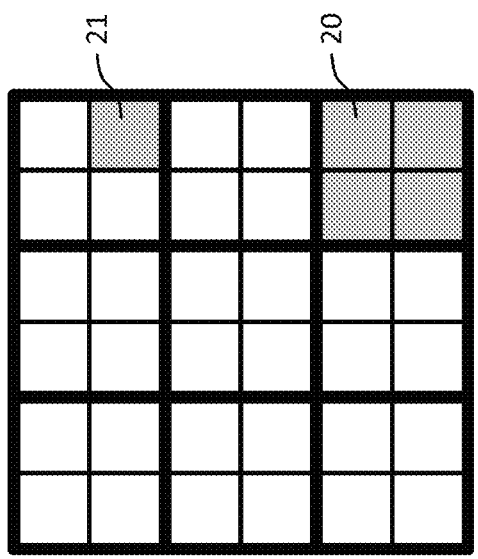
FIG. 4 illustrates an example of the relationship between an array of sensing elements and pixels of the X-ray detector relating to the first embodiment of the present invention.

Therefore, in the X-ray detector 150, the sub-pixels 21 detect the X-ray photons independently, and signals output from the multiple sensing elements 21 constituting each of the pixels 20, are added up to generate an output signal per pixel 20. FIG. 4 illustrates the pixels 20 where multiple sensing elements 21 each having the same size, are provided in the array with two elements in the channel direction and two elements in the slice direction, that is, four elements in total. In the example of FIG. 4, the size of the pixel 20 is one millimeter square and the size of each sub-pixel is 0.5 millimeter square, for instance. Following description of the present embodiment will be given, assuming that the pixel 20 comprises four sub-pixels 21.

In the present embodiment, the size of the pixel 20 is one millimeter square, and each pixel is divided into four sub-pixels with 0.5 millimeter square each. Other division patterns may be available variously, such as nine sub-pixels of 3×3, or 16 sub-pixels of 4×4. Alternatively, the vertical and horizontal directions may have different division numbers, like n×m (n and m are natural numbers).

The sub-pixels thus divided are not necessarily the same in size, and the present invention is applicable to the case where the pixel is divided into sub-pixels various in size. It is to be noted that the present invention is applicable to the case where the pixel is not divided into the sub-pixels. In this case, the "sub-pixel" in the following description will be read as "pixel".

Figure 5:
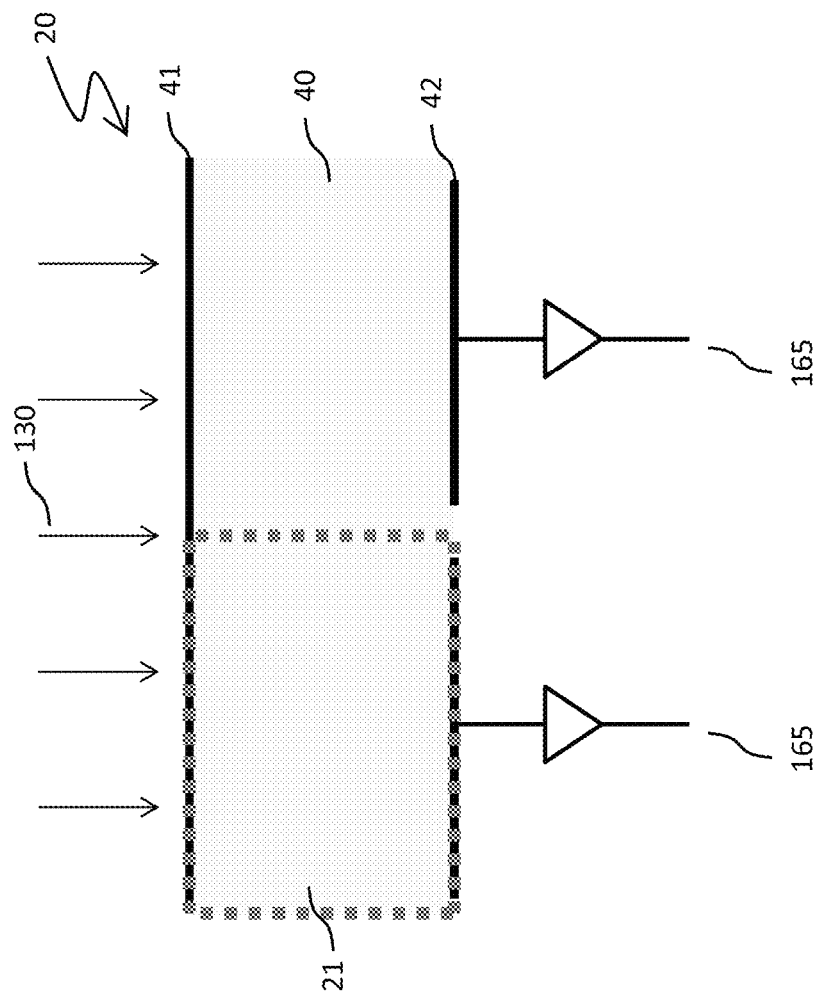
FIG. 5 illustrates an example of the relationship between the array of sensing elements and the pixel of the X-ray detector relating to the first embodiment of the present invention.

For example, as shown in FIG. 5, each of the sensing elements 21 constituting each pixel 20 has a structure provided with positive and negative electrodes 41 and 42 in a manner placing a detection layer 40 therebetween, and the signal processor 152 is connected to each of the electrodes 41 and 42. In the present embodiment, the negative electrode 41 (hereinafter, referred to as "common electrode 41") provided on the entrance surface of the X-ray photons 130 (the upper surface of the detection layer 40 in FIG. 5) serves as the common electrode covering the pixels 20 entirely. In addition, the positive electrode 42 (hereinafter, referred to as "individual electrode 42") is provided for each sensing element 21 serving as the sub-pixel, and individual channels 165 of the signal processor 152 are connected to the individual electrodes 42 respectively. In other words, signals are read per sub-pixel, thereby counting the X-ray photons including acquisition of energy information.

As described above, the pixels 20 are provided with one common electrode 41 and the individual electrodes 42 the number of which corresponds to the number of the sub-pixels 21 (sensing elements). In other words, the pixel 20 includes multiple individual electrodes 42 on the surface of the detection layer 40, and as indicated by broken lines in FIG. 5, a region associated with one individual electrode 42 forms one sub-pixel 21. As illustrated in FIG. 5, if a radiation detector material of a direct conversion type is used as the detection layer 40, boundaries between sub-pixels 21 (see FIG. 4) may be invisible physically when viewed from the top of the pixel 20, but the detection layer is divided into the sub-pixels, to function as the radiation detector.

It is preferable to employ as a material of the detection layer 40, a compound semiconductor being a radiation detector material of a direct conversion type, which is easy to micro machining and capable of direct reading of electrical signals, such as Cadmium Telluride, Cadmium Zinc Telluride, Thallium Bromide, Mercury Iodide, and Bismuth Iodide. Alternatively, a scintillator (a radiation detector material of a indirect conversion type) optically coupled with an optical device may be used as the detection layer. Preferably, the thickness of the detection layer is around 0.5 mm to 3 mm.

The X-ray photons 130 enter the detection layer 40 from the common electrode 41 side, then the X-ray photons being detected, and an electrical charge whose amount is responsive to the energy of thus detected X-ray photons is generated. The high-voltage power source, not illustrated, applies voltage of −600 V to the common electrode 41, for instance. It is desirable that there should be no attenuation of X-ray photons by the common electrode 41 or by the individual electrodes 42. The common electrode 41 and the individual electrodes 42 should be sufficiently thinner than the detection layer 40, and they may be processed to 1 µm or less in thickness.

Figure 6:
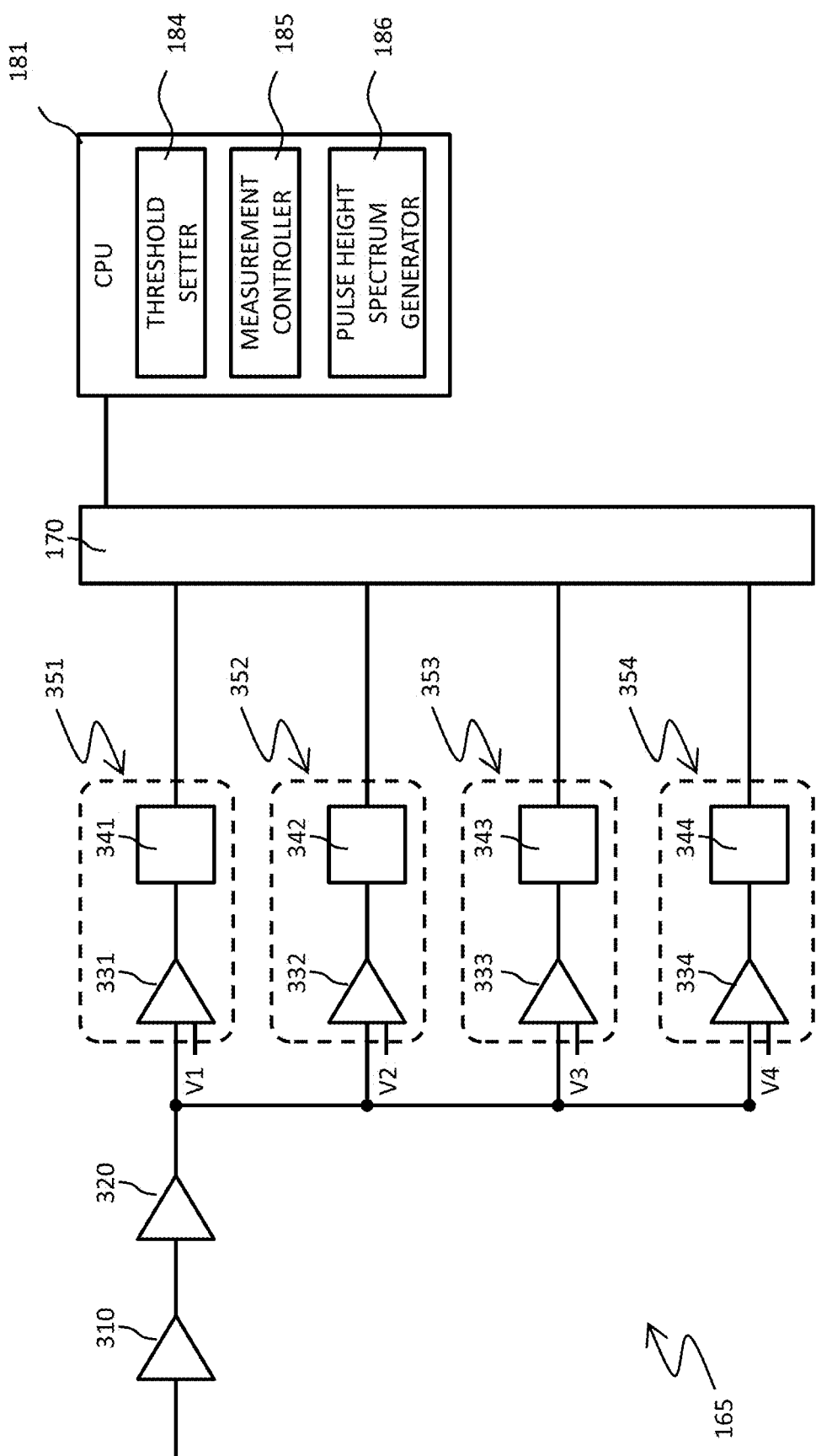
FIG. 6 is a block diagram showing a schematic configuration of a signal processor of the X-ray detector relating to the first embodiment of the present invention.

As shown in FIG. 6, the signal processor 152 is provided with channels 165 respectively for sub-pixels 21, and the channels 165 detect output signals from the sub-pixels 21 belonging to the pixel 20. Then, a signal adder adds up the signals according to predetermined conditions, collects the signals as an output signal from each pixel 20, and processes thus obtained output signal.

FIG. 6 illustrates an example of the channels 165 of the signal processor 152, being connected to the sub-pixels 21, respectively. Each of the channels 165 is provided with a charge sensitive pre-amplifier 310 configured to convert the X-ray photons detected as charge signals into voltage signals, a shaping amplifier 320 configured to perform shaping of the voltage signals converted by the charge sensitive pre-amplifier 310, and four counting units 351 to 354 to obtain energy information by comparing the voltage related to the voltage signal and thresholds (reference voltages). The counting units 351 to 354 are provided with converters 331 to 334, and counters 341 to 344, respectively.

Signal processing in the channel 165 as thus configured is performed as the following. A signal read out from any of the sub-pixels in the pixel 20, is initially converted into a voltage signal from a charge signal, by the charge sensitive pre-amplifier 310, and output to the shaping amplifier 320. The voltage signal converted by the charge sensitive pre-amplifier 310 is subjected to shaping in the shaping amplifier 320 (hereinafter, the voltage signal after the shaping will be referred to as "detected signal"), and in order to obtain the energy information, signals having a pulse height equal to or larger than thresholds (reference voltages) are counted in the counting units 351 to 354.

In FIG. 6, four comparators 331 to 334 are provided to obtain the energy information, and thresholds V1 to V4, different from one another are given to the comparators, respectively. Then, in the comparators 331 to 334, the detected signal is compared with the thresholds V1 to V4. When the detected signal is larger than the threshold, any of the counters 341 to 344 corresponding to the comparator is incremented.

With this configuration, the X-ray photons can be categorized into four types and counted separately, in response to the energy amount. After the elapse of predetermined processing time from the detection of an event by a trigger circuit, not illustrated, the individual channels 165 in the signal processor 152 are reset to become ready for the counting of next event. Upon completion of a predetermined measuring time (one view), incrementing is stopped, and the count rate of each counter is output to the controller 170. In designing the present embodiment, any number of the comparators, at least two, may be employed.

(Calibration in Counting Unit)

The thresholds V1 to V4 given to the comparators 331 to 334 respectively are able to supply the same voltage to a plurality of sub-pixels. However, due to the characteristics of the detection layer, or of the individual channels 165 (including the characteristics of the comparators 341 to 344) in the signal processing circuit, the same threshold may be associated with a different energy amount, as to each counting unit. In other words, though the same thresholds are provided, the same count results may not be obtained in some cases, as to each of the counting unit (even though impact of statistical errors is excluded). In such a case, it is preferable to perform calibration for each counting unit.

In performing calibration, X-rays or gamma-rays having characteristic energy is made to enter, and a pulse height spectrum is obtained in response to each threshold setting. Preferable examples of the X-rays or gamma-rays having characteristic energy may include line gamma-ray or characteristic X-ray, specifically, gamma-rays of 60 keV emitted from $^{241}$Am, gamma-rays of 122 keV emitted from $^{57}$Co, characteristic X-rays of 31 and 35 keV emitted from $^{133}$Ba, and characteristic X-rays of 75 keV and 85 keV emitted from lead irradiated with radiation. In addition to the line gamma-ray or characteristic X-ray, there are examples of the characteristic energy, such as Compton edge or a back scattering peak of such line gamma-ray or characteristic X-ray, and maximum energy of the X-ray photons determined by the tube voltage applied to the X-ray tube.

If non-linearity between the detected energy and output pulse height is not ignorable, it is preferable to render the characteristic energy held by the incident X-rays or gamma-rays to fall into the range, as close as possible to the energy range that is targeted for calibration.

Figure 7:
FIG. 7 is a reference diagram showing an example of a pulse height spectrum that is obtained when gamma rays are incident.

FIG. 7 shows an example of the pulse height spectrum that is obtained with the entry of gamma-rays from $^{57}$Co. According to the pulse height spectrum as shown in FIG. 7, it can be read that the photo peak of 122 keV is associated with the threshold setting to 47. If it is known that 60 keV is associated with the threshold setting to 23 in another measurement, it is found according to interpolation therebetween, that the threshold can be set to 31 for the counting an event of 80 keV or larger, whereby calibration of the counting units 351 to 354 can be achieved.

It is not necessary to acquire the pulse height spectrum of the whole energy range (or the whole threshold range), but it may be acquired as to a range only in proximity to the characteristic energy of incident X-rays or gamma-rays. For example, in the example as described above, even in the case where the pulse height spectrum is acquired only within the range where the threshold setting is from 40 to 55, it is possible to obtain what value of the threshold setting is associated with the photo peak of 122 keV.

(Acquisition of Pulse Height Spectrum)

Figure 8:
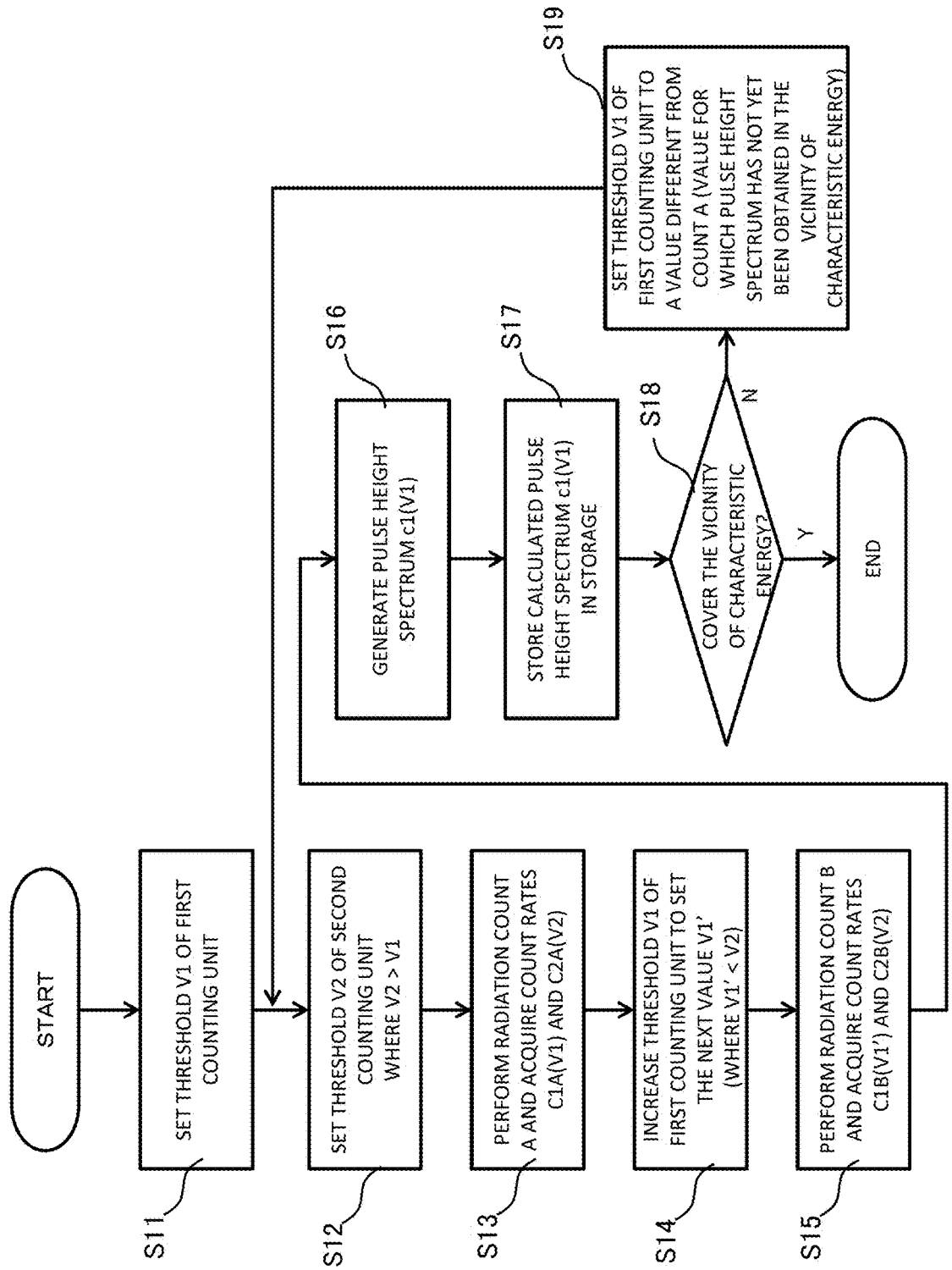
FIG. 8 is a flowchart to acquire the pulse height spectrum of the PCCT scanner relating to the first embodiment of the present invention.

The pulse height spectrum generator 186 generates the pulse height spectrum for each of the counting units 351 to 354. There will now be described how the pulse height spectrum is generated for the counting unit 351 (hereinafter, referred to as "first counting unit 351"). In the present embodiment, when the pulse height spectrum of the first counting unit 351 is acquired, the count rate (count value) of the counting unit 352 (hereinafter, referred to as "second counting unit 352") adjacent to the first counting unit 351 is also utilized. In the present embodiment, there has been described an example where the number of counting units is four, but this number can be changed appropriately. Specifically, the pulse height spectrum is generated and acquired according to the flowchart of FIG. 8.

In step S11, the threshold setter 184 sets the threshold V1 to the first counting unit 351, and in step S12, sets the threshold V2 to the second counting unit 352. In other words, as the threshold for the measurement (COUNT) A, the threshold setter 184 sets the first threshold V1 to the first counting unit, and sets to the second counting unit, the second threshold V2 that is larger than the first threshold V1.

Subsequently in step S13, the measurement controller 185 generates a control signal used to perform COUNT A, and outputs the control signal to the controller 170. The controller 170 controls the gantry rotor 110, the X-ray source 120, the table 140, the X-ray detector 150, and other components, according to the control signal from the measurement controller 185, and performs COUNT A.

In next step S14, the threshold setter 184 reconfigures the first threshold of the first counting unit. That is, the threshold setter 184 performs reconfiguration to change the first threshold V1 of the first counting unit to the first threshold V1', to be used as the threshold for the measurement (COUNT) B. The threshold setter 184 performs this reconfiguration so that the first threshold V1' becomes a value smaller than the second threshold V2 and different from the first threshold V1, and leaves the second threshold V2 as it is. In step S15, the measurement controller 185 generates a control signal to perform COUNT B, and outputs the control signal to the controller 170. The controller 170 performs COUNT B according to the control signal from the measurement controller 185.

In step S16, the pulse height spectrum generator 186 generates a pulse height spectrum for the first threshold in the first counting unit 351, on the basis of a difference between the count rate from the first counting unit and the second counting unit obtained by COUNT A, and the count rate from the first counting unit and the second counting unit obtained by COUNT B.

Specifically, in the first counting unit 351, the pulse height spectrum c1 ($V1_n$) at the threshold $V1_n$ is obtained according to the following process. As described above, in steps S13 and S15, the measurement controller 185 employs the threshold $V2_m$, where $V2_m > V1_n$ for the second counting unit 352 that is connected to the same sub-pixel to which the first counting unit 351 is connected, and performs COUNT A and B with the following settings:

COUNT A: (V1, V2)=($V1_{n-1}$, $V2_m$)
COUNT B: (V1, V2)=($V1_n$, $V2_m$)

Figure 9:
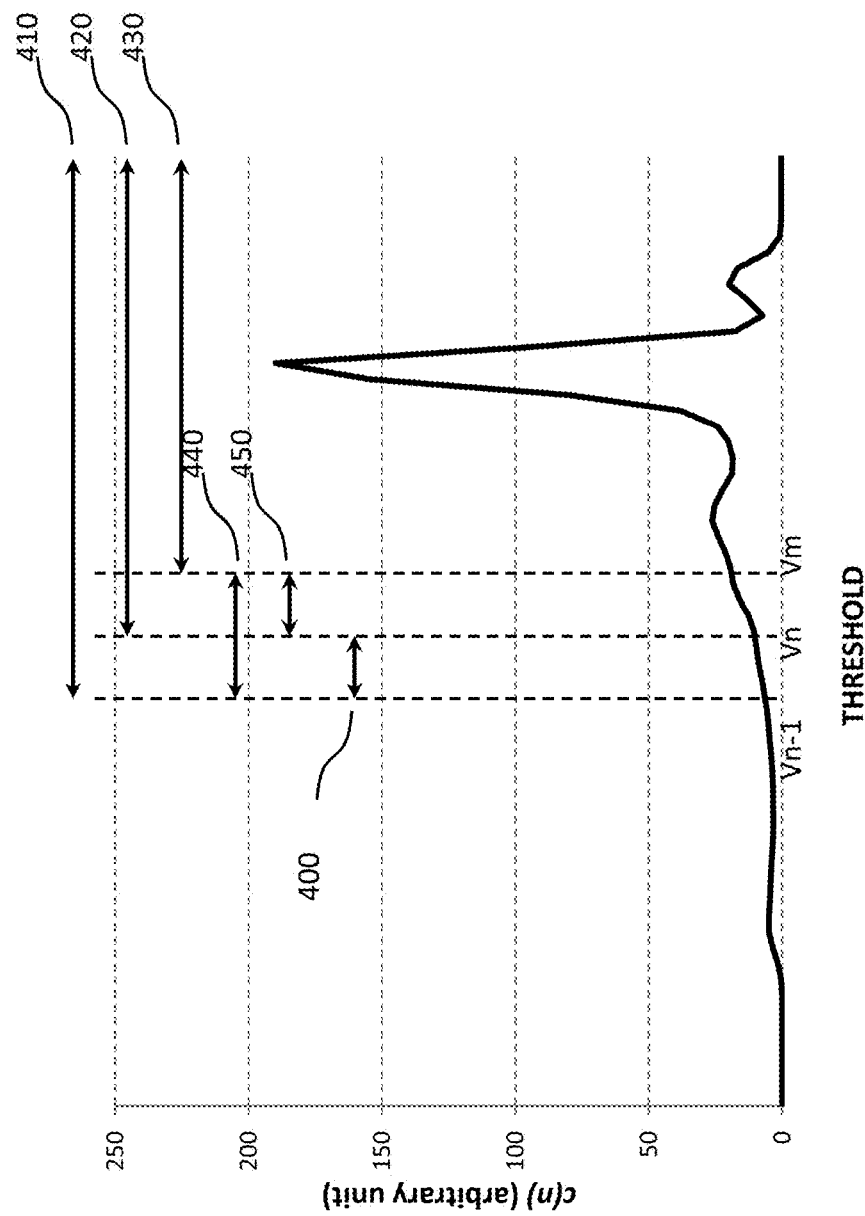
FIG. 9 is a reference diagram explicitly illustrating energy ranges on the pulse height spectrum of FIG. 7.

Assuming that expected values of the count rate C2 (V2$_m$) obtained in the second counting unit 352 should be the same in COUNT A and COUNT B described above, the pulse height spectrum c1 (V1$_n$) is obtained according to the following Equation 2. This corresponds to obtaining of the pulse height spectrum that is associated with the energy range 400, as shown in FIG. 9, using a difference between the count rate associated with the energy range 440 and the count rate associated with the energy range 450.

In here, Ctot denotes a total count rate (total number of counts per unit time), and Ctot is the same value irrespective of the counting units 351 to 354, in each of the channels 165 of one signal processor 152. In addition, C1 denotes the count rate obtained in the counting unit 351, and c1 denotes the pulse height spectrum of the counting unit 351. The count rate is obtained by normalizing the count value by the measuring time.

[2]

$$c1(V1_n) = (C1^{COUNTA}(V1_{n-1}) - C2^{COUNTA}(V2_m)) - (C1^{COUNTB}(V1_n) - C2^{COUNTB}(V2_m)) \quad (2)$$

$$= \left(\left[C_{tot}^{COUNTA} - \sum_{i=0}^{n-1} c1^{COUNTA}(V1_i)\right] - \left[C_{tot}^{COUNTA} - \sum_{i=0}^{m} c2^{COUNTA}(V2_i)\right]\right) -$$

$$\left(\left[C_{tot}^{COUNTB} - \sum_{i=0}^{n} c1^{COUNTB}(V1_i)\right] - \left[C_{tot}^{COUNTB} - \sum_{i=0}^{m} c2^{COUNTB}(V2_i)\right]\right)$$

$$= \left[\sum_{i=0}^{m} c2^{COUNTA}(V2_i) - \sum_{i=0}^{n-1} c1^{COUNTA}(V1_i)\right] - \left[\sum_{i=0}^{m} c2^{COUNTB}(V2_i) - \sum_{i=0}^{n} c1^{COUNTB}(V1_i)\right]$$

In step 17, thus obtained pulse height spectrum is stored in the storage unit 182. Then, in next step S18, it is determined whether the pulse height spectrum covering a targeted range is obtained. If it is determined it has not been obtained yet, the process proceeds with step S19 to reconfigure the first threshold, and processing from steps S12 to S18 is repeated. When it is determined in step S18 that the pulse height spectrum covering the targeted range is acquired, the process for acquiring the pulse height spectrum is completed.

On the other hand, in contrast to the pulse height spectrum thus obtained related to the present embodiment, the pulse height spectrum is obtained according to the following Equation 3 in the conventional method as disclosed in the aforementioned Patent Literature 1. In Equation 3, Ctot denotes the total count rate (the total number of counts per unit time), and the value of Ctot is the same, irrespective of the counting units 351 to 354, in each of the channels 165 of in one signal processor 152. This corresponds to obtaining of the pulse height spectrum that is associated with the energy range 400, as shown in FIG. 9, by using a difference between the count rate associated with the energy range 410 and the count rate associated with the energy range 420. In addition, C1 denotes the count rate obtained in the counting unit 351, and c1 denotes the pulse height spectrum of the counting unit 351. The count rate is obtained by normalizing the count value by the measuring time.

[3]

$$c1(V1_n) = C1^{COUNTA}(V1_{n-1}) - C1^{COUNTB}(V1_n) \quad (3)$$

$$= \left[C_{tot}^{COUNTA} - \sum_{i=0}^{n-1} c1^{COUNTA}(V1_i)\right] - \left[C_{tot}^{COUNTB} - \sum_{i=0}^{n} c1^{COUNTB}(V1_i)\right]$$

Next, there will be described that the measuring time can be reduced according to the method of the present embodiment for generating the pulse height spectrum. There will be described an example where the count rate C1(V1$_{n-1}$) (associated with the energy range 410 in FIG. 9) is 100 cps when the threshold of the counting unit 351 is set to V1$_{n-1}$, the count rate C1(V1$_n$) (associated with the energy range 420 in FIG. 9) is 90 cps when this threshold is set to V1$_n$, and the count rate C2(V2$_m$) (associated with the energy range 430 in FIG. 9) is 80 cps when the threshold of the counting unit 352 is set to V2$_m$. When the measurement is performed for one second, an expected value of the pulse height spectrum c1(V1$_n$) for the energy range 400 becomes 10 counts according to both the conventional method and the present embodiment. On the other hand, a degree of accuracy of c1(V1$_e$) is calculated as the following, according to the Poisson distribution.

[4]

$\sqrt{100+90}$=13.8 COUNT      Conventional Method $\sqrt{(100-80)+(90-80)}$=5.5 COUNT      Present Embodiment According to the calculation above, it was confirmed that the degree of accuracy became 2.5 times larger (13.8/5.5=2.5) in the example of the present embodiment. In general, the accuracy in measurement is proportional to the square of the measuring time, and therefore, it is found that only one-six or less measuring time is required to achieve the same level of accuracy.

When the pulse height spectrum is obtained according to the conventional method, one time measurement is performed for each threshold to detect a difference between the count rates of the thresholds. On the other hand, when the method for generating the pulse height spectrum according to the present embodiment is employed, it is necessary to perform two times measurement, COUNT A and COUNT B, for the threshold V1$_n$ in the counting unit 351, with setting threshold V2$_n$ larger than V1$_n$ to the other counting unit 352, resulting in that the number of measuring times is doubled at the maximum, in comparison to the conventional method. Therefore, it is desirable to set V2$_m$ to be a value close to V1$_n$, making C2(V2$_m$) be a large value so that the whole measurement may require less time. Conditions to achieve higher accuracy in the measurement of the present embodiment, even with the doubled measurement, can be provided assuming a situation that doubled measuring time can be consumed for the conventional method, and it is calculated according to the following expression 4.

[5]

$$\frac{\sqrt{C1(V1_{n-1})\times 2t + C1(V1_n)\times 2t}}{C1(V1_{n-1})\times 2t - C1(V1_n)\times 2t} > \frac{\sqrt{\left(\frac{C1(V1_{n-1})-}{C2(V2_m)}\right)\times t + \left(\frac{C1(V1_n)-}{C2(V2_m)}\right)\times t}}{\left(\frac{C1(V1_{n-1})-}{C2(V2_m)}\right)\times t - \left(\frac{C1(V1_n)-}{C2(V2_m)}\right)\times t} \quad (4)$$

$$C2(V2_m) > \frac{C1(V1_{n-1}) + C1(V1_n)}{4}$$

Assuming that $C1(V1_{n-1})$ is approximately equal to $C1(V1_n)$, it is preferable to set $V2_m$ so that $C2(V2_m)$ is equal to or larger than a half of $C1(V1_n)$ (to set $V2_m$ to be a value close to $V1_n$).

The measuring time may be provided to different thresholds independently. Under the condition that the pulse height spectrum is given accuracy being required, necessary measuring time can be obtained in response to the count rates $C1(V1)$ and $C2(V2)$, or in response to a difference therebetween. This is preferable since the total measuring time can be reduced, by setting the measuring time flexibly depending on the values of the thresholds.

In obtaining the count rates $C(V)$ by COUNT A and COUNT B, it should be noted that the counting is required to be normalized based on live time (the time obtained by subtracting dead time in measurement system, from the actual measuring time), not based on the actual measuring time. For this purpose, in the case where the same actual measuring time should be provided for COUNT A and COUNT B, it is preferable to carry out the measurement under the same trigger condition, so as to achieve the same dead time. Alternatively, it is preferable to carry out the measurement at a low count rate to the extent that the dead time is ignorable, for example, 1% or less.

In reality, the same value of $V2_m$ is provided to multiple $V_n$ as to which the pulse height spectrum is required to obtain, thereby lessening the number of measurements to reduce the measuring time. For example, with the setting of $(V1, V2)=(V1_{n-2}, V2_m), (V1_{n-1}, V2_m)$, and $(V1_n, V2_m)$, the measurement can be performed three times. The case is preferable because two pulse height spectra $c1(V1_{n-1})$ and $c1(V1_n)$ respectively associated with $V1_{n-1}$ and $V1_n$ can be obtained according to the measurement of three times, and this may prevent increase of the number of measurements.

(Acquisition of Pulse Height Spectrum of Other Counting Units)

As described above, it is necessary to obtain the pulse height spectrum of each counting unit. In the aforementioned example, there has been described the method for acquiring the pulse height spectrum of the counting unit 351. According to the same procedures as described in the aforementioned method, the pulse height spectrum can be obtained for other counting units within a short amount of time. In the present embodiment, in order to reduce the measuring time, four counting units are respectively provided with the thresholds V1 to V4 and the measurements are performed, so as to obtain the pulse height spectra.

Figure 10:
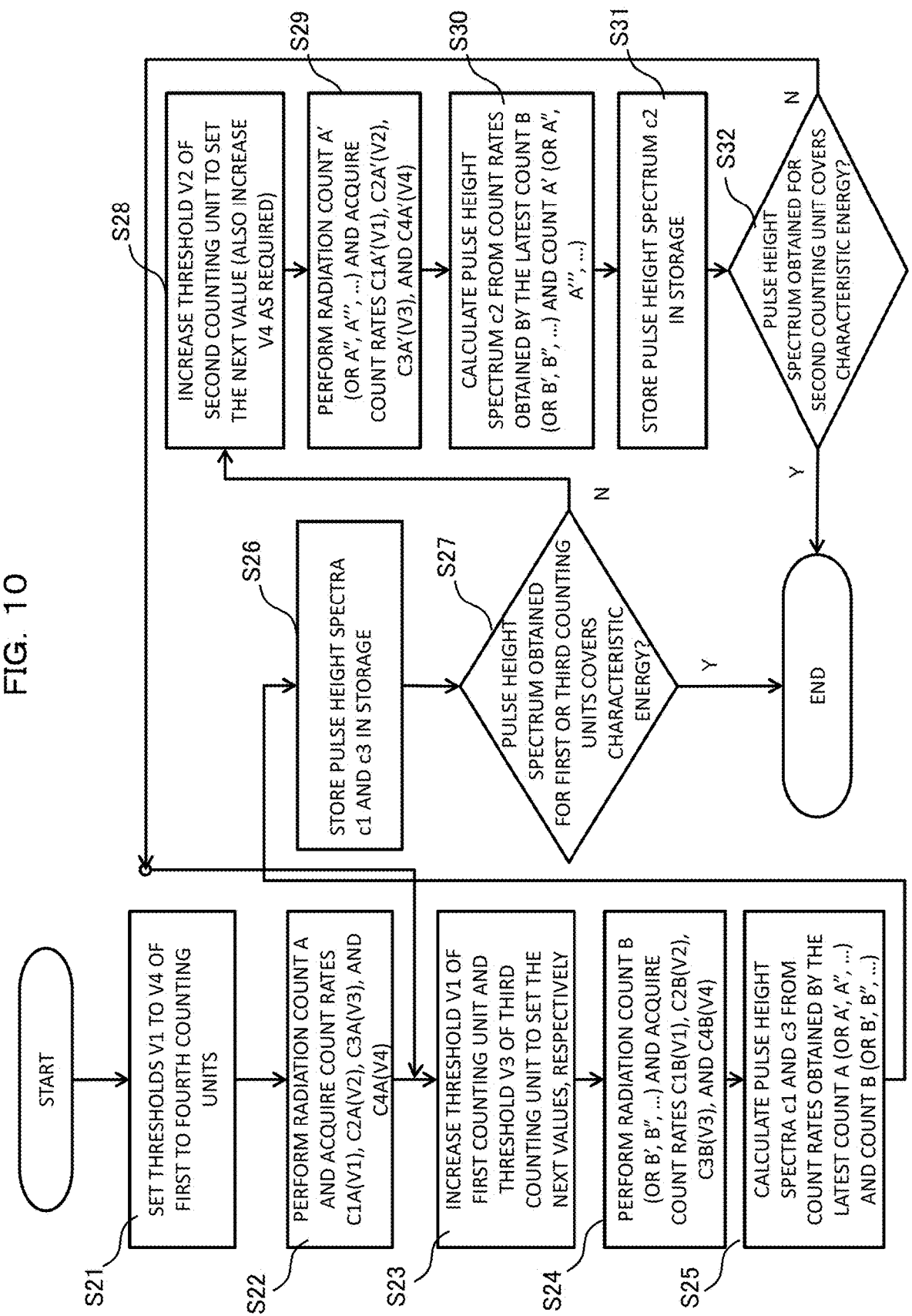
FIG. 10 is another flowchart to acquire the pulse height spectrum of the PCCT scanner relating to the first embodiment of the present invention.

This type of pulse height spectrum can be acquired according to the flowchart of FIG. 10, for instance. In step S21, the threshold setter 184 sets the thresholds V1 to V4, different from one another, respectively to the first to the fourth counting units 351 to 354. In next step S22, the measurement controller 185 generates a control signal to perform COUNT A, and outputs the control signal to the controller 170. According to the control signal from the measurement controller 185, the controller 170 controls the gantry rotor 110, the X-ray source 120, the table 140, the X-ray detector 150, and other components, and performs COUNT A.

Then, in step S23, the threshold setter 184 increases the threshold V1 of the first counting unit 351 and the threshold V3 of the third counting unit 353 to reconfigure the thresholds as the next values. According to thus reconfigured thresholds, the measurement controller 185 performs COUNT B in step S24. In step S25, the pulse height spectra are acquired from the count rate obtained by COUNT A and COUNT B, and the storage unit 182 stores thus acquired pulse height spectra (step S26). It is determined whether or not thus acquired pulse height spectra cover target ranges. On the other hand, when it is determined that such pulse height spectra have not been acquired yet, the process proceeds with step S28. When it is determined that the pulse height spectra covering the target ranges have been obtained in step S27, the process for acquiring the pulse height spectra is completed.

In step S28, the threshold V2 of the second counting unit 352 is increased and reconfigured as the next value. At this time, the threshold V4 of the fourth counting unit 354 may also be increased as needed. In next step S29, according to the threshold set in step S28, COUNT A' is performed. Then, in step S30, the pulse height spectrum generator 186 generates the pulse height spectrum on the basis of the count rate obtained from the latest two measurements, and the storage unit 182 stores the pulse height spectrum generated in step S31. In next step S32, it is determined whether or not the pulse height spectrum covering the target range is obtained, and if it is determined that such pulse height spectrum has not been acquired, the process proceeds with step S23, and the processing from steps S23 to S32 is repeated. When it is determined that the pulse height spectra covering the target ranges have been obtained in step S27 or S32, the process for acquiring the pulse height spectra is completed.

The relations between the aforementioned thresholds and measurements are summarized, and followings are established between the thresholds V1 to V4 set to the four counting units, and the measurements (COUNTs):

COUNT A: (V1, V2, V3, V4)=($V1_{n-1}$, $V2_{m-1}$, $V3_{p-1}$, $V4_{q-1}$)
COUNT B: (V1, V2, V3, V4)=($V1_n$, $V2_{m-1}$, $V3_p$, $V4_{q-1}$)
COUNT A': (V1, V2, V3, V4)=($V1_n$, $V2_m$, $V3_p$, $V4_q$)
COUNT B': (V1, V2, V3, V4)=($V1_{n+1}$, $V2_m$, $V3_{p+1}$, $V4_q$)
...
where V1<V2<V3<V4

The pulse height spectra calculation process in steps S25 and S30 is performed according to the following Equation 5, from the count rate C each obtained from the measurements (COUNTs) described above. In other words, according to Equation 5, the pulse height spectra of the first counting unit 351 to the third counting unit 353 can be obtained efficiently. As for the counting unit 354, the pulse height spectrum may be obtained from the measurement using the aforementioned method separately.

[6]

$$c1(V1_n) = (C1^{COUNTA}(V1_{n-1}) - C2^{COUNTA}(V2_{m-1})) - (C1^{COUNTB}(V1_n) - C2^{COUNTB}(V2_{m-1}))$$

$$c1(v1_{n+1}) = (C1^{COUNTA'}(V1_n) - C2^{COUNTA'}(V2_m)) - (C1^{COUNTB'}(V1_{n+1}) - C2^{COUNTB'}(V2_m))$$

$$c2(V2_m) = (C2^{COUNTB}(V2_{m-1}) - C3^{COUNTB}(V3_p)) - (C2^{COUNTA'}(V2_m) - C3^{COUNTA'}(V3_p))$$

$$c3(V3_p) = (C3^{COUNTA}(V3_{p-1}) - C4^{COUNTA}(V4_{q-1})) - (C3^{COUNTB}(V3_p) - C4^{COUNTB}(V4_{q-1}))$$

$$c3(V3_{p+1}) = (C3^{COUNTA'}(V3_p) - C4^{COUNTA'}(V4_q)) - (C3^{COUNTB'}(V3_{p+1}) - C4^{COUNTB'}(V4_q)) \quad (5)$$

The threshold V4 of the counting unit 354 is not necessarily incremented by one, such as $V_{q-1}$, $V_q$, and $V_{q+1}$. For example, even though the threshold V4 can be a value sufficiently larger value than the value of V3, it is desirable to vary the value of the threshold V4 gradually following the variation of V3 as given by the aforementioned Equation, in light of an objective of the present embodiment, i.e., "to reduce the measuring time by mitigating errors with narrowing the energy range 450".

As described so far, the simple configuration is provided as shown in FIG. 6, holding less number of parameters, such as four thresholds for four counting units, and generating a highly accurate pulse height spectra in a short amount of time with calibration of the detector, whereby the radiation detector or the radiation imaging apparatus can be implemented at low cost.

Second Embodiment

Next, there will be described the PCCT scanner according to a second embodiment of the present invention. In the following, components of the PCCT scanner identical to the first embodiment will be labeled the same, and will not be described redundantly.

(Operation of Signal Processor)

Figure 11:
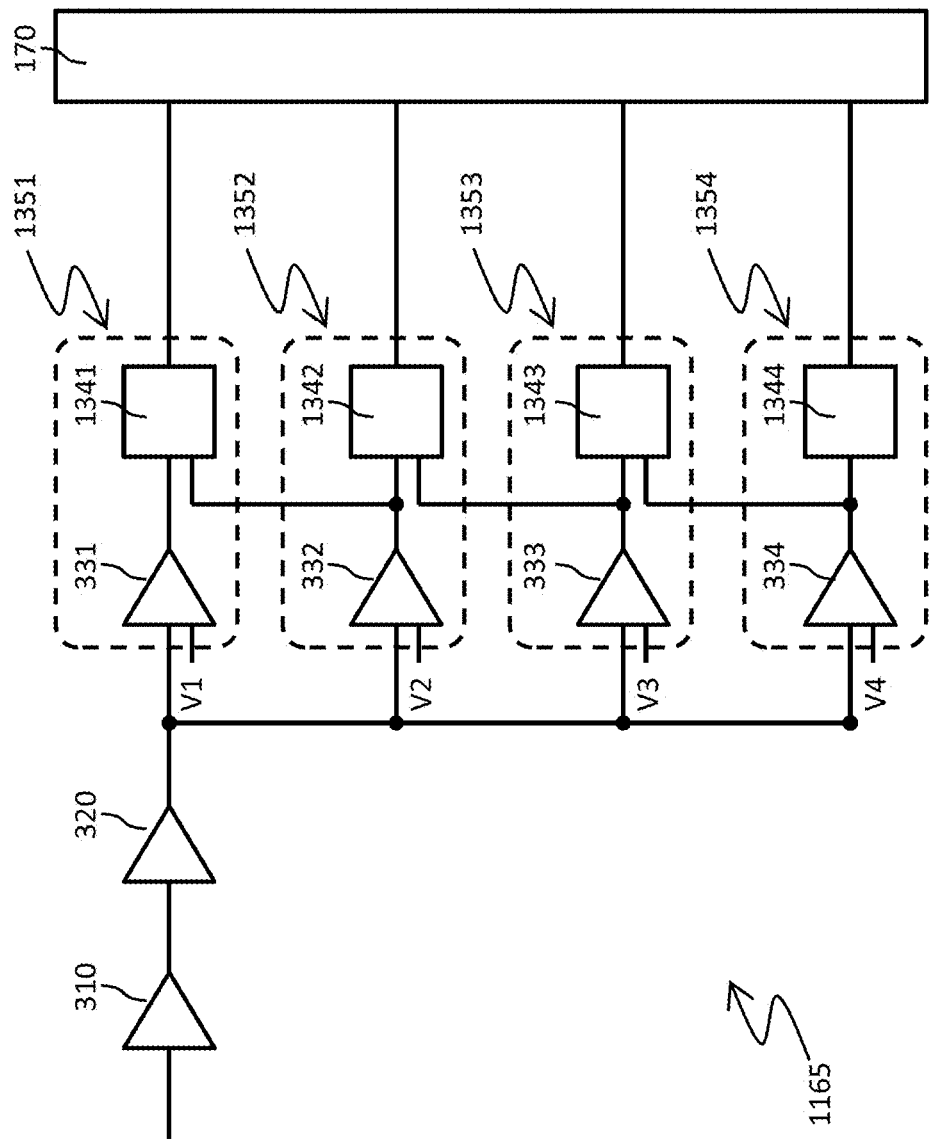
FIG. 11 is a block diagram showing a schematic configuration of the signal processor of the X-ray detector relating to a second embodiment of the present invention.

In the second embodiment, the operation of the processing circuit is different from the first embodiment. FIG. 11 illustrates an example of an individual channel 1165 connected to each sub-pixel of the signal processor 152. A signal output from the shaping amplifier 320 is counted in response to a result of comparison of the pulse height, larger or smaller than a threshold (reference voltage), in each of the counting units 1351 to 1354.

Specifically, in the counting unit 1351, there are counted a signal having the pulse height between the threshold V1 and V2, in the counting unit 1352, a signal having the pulse height between the thresholds V2 and V3, in the counting unit 1353, a signal having the pulse height between the threshold V3 and V4, and in the counting unit 1354, a signal having the pulse height equal to or larger than the threshold V4. It is to be noted here that the thresholds are configured in a manner that satisfies V1<V2<V3<V4.

For example, when the pulse height is between the threshold V2 and V3, the signal is output from the comparators 331 and 332, but not from the comparators 333 and 334. Since there is an entry of the signal in the counter 1341, coming from both of the comparators 331 and 332, it can be determined that the original signal does not have the pulse height between the thresholds V1 and V2, and this event is not counted in the counter 1341.

Since the signal only from the comparator 332, but not from the comparator 333, enters the counter 1342, it can be determined that the original signal has the pulse height between the threshold V2 and V3, and this event is counted in the counter 1342. It is to be noted here in FIG. 11, there are provided four comparators 331 to 334 in order to obtain the energy information, but any number of the comparators, at least two, may be used in designing the present embodiment.

(Acquisition of Pulse Height Spectrum)

Let D1 denote the count rate obtained in the counting unit 1351, and this value is related to the count rate obtained in the configuration of the first embodiment, as given in the following:

[7]
$$D1(V1,V2) = C1(V1) - C2(V2) \quad (6)$$

Therefore, in order to acquire the pulse height spectrum $c1(V1_n)$ at the threshold $V1_n$, the threshold $V2_m$ satisfying $V2_m > V1_n$ is employed, similar to the first embodiment, and the measurement (COUNT) is performed with the settings as the following:

COUNT A: $(V1, V2) = (V1_{n-1}, V2_m)$
COUNT B: $(V1, V2) = (V1_n, V2_m)$ By using the count rate as obtained by the measurements, the pulse height spectrum $c1(V1_n)$ can be obtained by the following Equation, and a similar effect can be achieved:

[8]
$$c1(V1_n) = D1^{COUNTA}(V1_{n-1}, V2_m) - D1^{COUNTB}(V1_n, V2_m) \quad (7)$$

In addition to the aforementioned embodiments, a difference between the counting results obtained in the two counting units may be calculated and output in the controller 170, unlike the second embodiment where the outputs from the two comparators are input in one counter, and this enables implementation of the same function as the second embodiment.

In the present embodiment, the value of n is made to vary, one by one, to obtain the pulse height spectrum, but modification is possible such as varying the value of n, two by two, depending on how much density is required in obtaining the pulse height spectrum.

Further in the present embodiments, the sub-pixels are separated, by providing the common electrode on the upper surface of the radiation detector material of a direct conversion type, with the individual electrodes on the lower side thereof.

However, the sub-pixels may be provided with the individual electrodes also on the upper surface, without using the common electrode. Similarly, in a plurality of radiation detectors, the pixels 20 in the radiation detectors adjacent to each other may share the common electrode on the upper surface, or may be provided with the electrodes individually.

As a material of the detector, it is also possible to employ a material comprising a scintillator (radiation detector material of an indirect conversion type) optically coupled with an optical device, instead of the radiation detector material of a direct conversion type. In this case, as a method for separating the sub-pixels, the scintillator covered with a light-shielding agent may be provided for each sub-pixel. Alternatively, for one scintillator, a method for producing micro-cracks between sub-pixels by laser may be used to separate the sub-pixels. As the optical device, a photomultiplier tube (PMT), photodiode (PD), avalanche photodiode (APD), silicone photomultiplier (SiPM), and similar elements may be employed.

DESCRIPTION OF SYMBOLS

20 . . . pixel, 21 . . . sub-pixel, 40 . . . detection layer, 41, 42 . . . electrode, 110 . . . gantry rotor, 120 . . . X-ray source, 125 . . . filter, 130 . . . X-ray photon, 140 . . . table, 145 . . . collimator, 150 . . . X-ray detector, 151 . . . detection unit, 152 . . . signal processor, 165 . . . channel, 170 . . . controller, 180 . . . computer, 181 . . . CPU, 182 . . . storage unit, 184 . . . threshold setter, 185 . . . measurement controller, 186 . . . pulse height spectrum generator, 191 . . . display unit, 192 . . . input unit

What is claimed is:

1. A pulse height spectrum acquisition device of a radiation detector including a plurality of counting units for counting a detected signal obtained by detecting incident X-rays, when a value of the detected signal is equal to or larger than a threshold, and for outputting a count value of each of the counting units, the pulse height spectrum acquisition device comprising,
a threshold setter configured to set a first threshold V1 to a first counting unit as a threshold for a first measurement, along with setting to a second counting unit, a second threshold V2 larger than the first threshold V1, and to set a reconfigured first threshold V1' to the first counting unit, as the threshold for a second measurement, the reconfigured first threshold being different from the first threshold V1,
a measurement controller configured to perform the first measurement and the second measurement, and
a pulse height spectrum generator configured to generate a pulse height spectrum for the first threshold V1 of the first counting unit, on the basis of a difference between the count value from the first counting unit and the second counting unit obtained by the first measurement performed by the measurement controller, and the count value from the first counting unit and the second counting unit obtained by the second measurement.

2. The pulse height spectrum acquisition device according to claim 1, wherein,
the first counting unit outputs the count value of the detected signal having a pulse height between the first threshold and the second threshold.

3. The pulse height spectrum acquisition device according to claim 1, wherein,
when the threshold setter reconfigures the first threshold, the reconfigured first threshold is set to be a value smaller than the second threshold.

4. The pulse height spectrum acquisition device according to claim 1, wherein,
the threshold setter sets the second threshold so that the count value of the detected signal having a pulse height equal to or larger than the second threshold, is equal to or larger than a half of the count value of the detected signal having the pulse height equal to or larger than the first threshold.

5. A radiation imaging apparatus comprising the pulse height spectrum acquisition device according to claim 1.

6. A pulse height spectrum acquisition method of a radiation detector including a plurality of counting units for counting a detected signal obtained by detecting incident X-rays, when a value of the detected signal is equal to or larger than a threshold, and for outputting a count value of each of the counting units, the pulse height spectrum acquisition method comprising,
setting a first threshold to a first counting unit, as a threshold for a first measurement, along with setting to a second counting unit, a second threshold larger than the first threshold, and setting a reconfigured first threshold to the first counting unit, as the threshold for a second measurement, the reconfigured first threshold being different from the first threshold,
acquiring the count values of the first counting unit and of the second counting unit, obtained by the first measurement and the second measurement, and
generating a pulse height spectrum for the first threshold of the first counting unit, on the basis of a difference between the count value from the first counting unit and the second counting unit obtained by the first measurement, and the count value from the first counting unit and the second counting unit obtained by the second measurement.

7. A pulse height spectrum acquisition program of a radiation detector including a plurality of counting units for counting a detected signal obtained by detecting incident X-rays, when a value of the detected signal is equal to or larger than a threshold, and for outputting a count value of each of the counting units, causing a computer to implement,
setting a first threshold to a first counting unit, as a threshold for a first measurement, along with setting to a second counting unit, a second threshold larger than the first threshold, and setting a reconfigured first threshold to the first counting unit, as the threshold for a second measurement, the reconfigured first threshold being different from the first threshold,
acquiring the count values of the first counting unit and of the second counting unit, obtained by the first measurement and the second measurement, and
generating a pulse height spectrum for the first threshold of the first counting unit, on the basis of a difference between the count value from the first counting unit and the second counting unit obtained by the first measurement, and the count value from the first counting unit and the second counting unit obtained by the second measurement.

* * * * *